United States Patent [19]

Shibasaki et al.

[11] Patent Number: 5,117,037

[45] Date of Patent: May 26, 1992

[54] CIS-BICYCLO(4,3.0)NON-2-ENE DERIVATIVES

[75] Inventors: Masakatsu Shibasaki, Sapporo; Takahashi Atsuo, Fukushima; Tuyoshi Aoki, Fukushima; Hiroyasu Sato, Fukushima; Shin-ichi Yamada, Fukuchima; Michiko Kudo, Fukushima; Takaji Yamaguchi, Fukushima; Kentaro Kogi, Shiroishi; Sen-ichi Narita, Tokyo, all of Japan

[73] Assignee: Sagami Chemical Research Center Toa Eiyo Ltd., Tokyo, Japan

[21] Appl. No.: 622,471

[22] Filed: Dec. 5, 1990

[30] Foreign Application Priority Data

Dec. 5, 1989 [JP] Japan .................... 1-314338
Oct. 19, 1990 [JP] Japan .................... 2-279196

[51] Int. Cl.$^5$ .................................. C07C 177/00
[52] U.S. Cl. ........................... 560/53; 560/56; 560/119; 562/462; 562/466; 562/501
[58] Field of Search ............ 560/119, 53, 56; 562/501, 462, 466

[56] References Cited

U.S. PATENT DOCUMENTS

| | | | |
|---|---|---|---|
| 4,699,921 | 10/1987 | Shihasaki | 560/119 |
| 4,730,060 | 3/1988 | Tomiyama | 560/119 |
| 4,954,524 | 9/1990 | Skuballa | 560/119 |
| 4,971,987 | 11/1990 | Vorbrueggen | 560/119 |
| 5,053,526 | 10/1991 | Shibasaki | 560/119 |

FOREIGN PATENT DOCUMENTS

| | | |
|---|---|---|
| 3226550 | 1/1984 | Fed. Rep. of Germany . |
| 2201841 | 9/1987 | Japan . |
| 3141943 | 8/1988 | Japan . |
| 3216842 | 9/1988 | Japan . |
| 2178252 | 7/1990 | Japan . |

2129427  5/1984  United Kingdom .

Primary Examiner—Paul J. Killos
Attorney, Agent, or Firm—Oblon, Spivak, McClelland, Maier & Neustadt

[57] ABSTRACT

A cis-bicyclo[4.3.0]non-2-ene derivative of the formula:

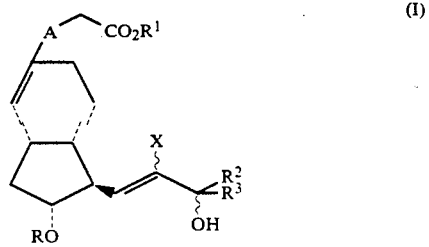

wherein R is a hydrogen atom, or a protecting group for a hydroxyl group, $R^1$ is a hydrogen atom, A $C_1$-$C_{12}$ straight or branched chain alkyl group, a substituted or unsubstituted phenyl group, a $C_6$-$C_{12}$ aralkyl group containing a condensed aromatic ring or an aromatic hetero ring, or 1 equivalent of a cation, A is —CH=CH—$CH_2$—, or —$CH_2$—$CH_2$—O—, $R^2$ is a $C_3$-$C_{10}$ straight or branched chain alkyl group, a $C_1$-$C_3$ alkyl group substituted by an aryloxy group which may be substituted, a $C_3$-$C_{12}$ straight or branched chain alkenyl group, a $C_3$-$C_8$ straight or branched chain alkynyl group, a $C_1$-$C_3$ alkyl group substituted by a phenyl or phenoxy group which may be substituted, by a $C_1$-$C_6$ alkoxy group or by a $C_5$-$C_8$ cycloalkyl group, $R^3$ is a hydrogen atom, a methyl group, or a vinyl group, and X is a halogen atom.

2 Claims, No Drawings

CIS-BICYCLO(4,3.0)NON-2-ENE DERIVATIVES

The present invention relates to novel cis-bicyclo[4.3.0]non-2-ene derivatives which are useful as intermediates for prostacyclin analogues having platelet anti-aggregatory activities.

Prostagrandin (hereinafter referred to as PG) $I_2$ is known to be a natural physiologically active substance produced by vascular walls and leukocytes. $PGI_2$ has potent blood platelet anti-aggregatory activities and is used as an anti-thrombus agent for patients using pump-oxygenators or artificial dialysis. Further, it is considered to be useful also for the prevention and curing of an ischemic heart disease such as acute angina pectoris or myocardial infarction, a disturbance of cerebral circulation such as cerebral thrombosis or cerebral infarction, and a peripheral circulatory failure such as buerger or arteriosclerosis occlusion, induced by an increase of the thrombic tendency.

Further, it is known that PGs including $PGI_2$ have cytoprotecting activities and gastric mucosal blood-flow increasing activities in gastnic mucosa, and they been expected to be useful for the prevention and curing of a peptic ulcer such as gastric ulcer.

However, $PGI_2$ has an enol ether structure and is thus chemically very unstable. Not only that, it has rather strong undesirable physiological activities such as actions for diarrhea, uterine muscle contraction or hypotension. These are major problems which limit its application as a drug. To prepare a drug formulation which can be orally administered and which has continuous activities, as a drug, it is desired that the drug formulation is stable in the digestive tract without being decomposed. To solve such problems, many researches for $PGI_2$ analogues have been conducted in a wide range. From such researches, carbacyclin derivatives represented by OP-41483 (Japanese Unexamined Patent Publication No. 130543/1979) and isocarbacyclin (Japanese Unexamined Patent Publication No. 137445/1984) as well as homoisocarbacyclin derivatives (Japanese Unexamined Patent Publication No. 110644/1989) by the present inventors, have been developed as typical chemically stable derivatives.

Considering of $PGI_2$ derivatives at as drugs capable of being orally administered, prostacyclin anoalogues having a triple bond at the 1-position of the ω-chain among the compounds disclosed in the above mentioned Japanese Unexamined Patent Publication No. 110644/1989 are particularly excellent drugs in that they are stronger than $PGI_2$ in the platelet anti-aggregatory activities and yet exhibit continuous activities, and they are phisicochemically stable and excellent in the action selectivity having less side effects such as actions for diarrhea or uterine muscle contraction.

The present inventors have conducted a wide range of researches with an aim to provide $PGI_2$ analogues which are stable even in an acidic solution without being substantially decomposed at room temperature and which have excellent pharmacological properties. As a result, it has been found that the cis-bicyclo[4.3.0]-non-2-ene derivatives of the following formula (I) or (II) can be important intermediates for the production of the desired prostacyclin analogues. The present invention has been accomplished on the basis of this discovery.

Thus, the present invention provides a cis-bicyclo[4.3.0]non-2-ene derivative of the formula:

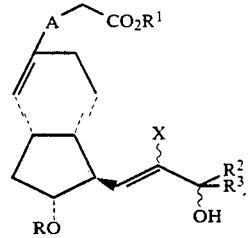

wherein R is a hydrogen atom, or a protecting group for a hydroxyl group, $R^1$ is a hydrogen atom, a $C_1$-$C_{12}$ straight or branched chain alkyl group, a substituted or unsubstituted phenyl group, a $C_6$-$C_{12}$ aralkyl group containing a condensed aromatic ring or an aromatic hetero ring, or 1 equivalent of a cation, A is —CH=CH—CH$_2$—, or —CH$_2$—CH$_2$—O—, $R^2$ is a $C_3$-$C_{10}$ straight or branched chain alkyl group, a $C_1$-$C_3$ alkyl group substituted by an aryloxy group which may be substituted, a $C_3$-$C_{12}$ straight or branched chain alkenyl group, a $C_3$-$C_8$ Straight or branched chain alkynyl group, or a $C_1$-$C_3$ alkyl group substituted by a phenyl or phenoxy group which may be substituted, by a $C_1$-$C_6$ alkoxy group or by a $C_5$-$C_8$ cycloalkyl group, $R^3$ is a hydrogen atom, a methyl group, or a vinyl group, and X is a halogen atom, and a cis-bicyclo[4.3.0]-non-2-ene derivative of the formula:

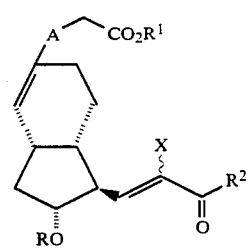

wherein R is a hydrogen atom, or a protecting group for a hydroxyl group, $R^1$ is a hydrogen atom, a $C_1$-$C_{12}$ straight or branched chain alkyl group, a Substituted or unsubstituted phenyl group, a $C_6$-$C_{12}$ aralkyl group containing a condensed aromatic ring or an aromatic hetero ring, or 1 equivalent of a cation, A is —CH=CH—CH$_2$—, or —CH$_2$—CH$_2$—O—, $R_2$ is a $C_3$-$C_{10}$ straight or branched chain alkyl group, a $C_1$-$C_3$ alkyl group substituted by an aryloxy group which may be substituted, a $C_3$-$C_{12}$ straight or branched chain alkenyl group, a $C_3$-$C_8$ straight or branched chain alkynyl group, or a $C_1$-$C_3$ alkyl group substituted by a phenyl or phenoxy group which may be substituted, by a $C_1$-$C_6$ alkoxy group or by a $C_5$-$C_8$ cycloalkyl group, and X is a halogen atom.

Now, the present invention will described in detail with reference to the preferred embodiments.

In the above formulas (I) and (II), the $C_1$-$C_{12}$ straight or branched chain alkyl group for $R^1$ includes, for example, methyl, ethyl, n-propyl, iso propyl, n-butyl, sec-butyl, tert-butyl, n-pentyl, iso-amyl, n-nonyl, n-decyl, n-undecyl and n-dodecyl.

As the substituent for the substituted phenyl group for $R^1$, a halogen atom, a hydroxyl group, a $C_2$-$C_7$ acyloxy group, a $C_1$-$C_4$ alkyl group which may be substituted by a halogen atom, a $C_1$-$C_4$ alkoxy group which may be substituted by a halogen atom. a nitrile group, a carboxyl group, a $C_2$-$C_7$ alkocarboxyl group, or a carbamoyl group which is subslituted by a $C_1$-$C_{10}$ alkyl or aryl group, is for example preferred. Here, the halogen atom may be fluorine, chlorine or bromine, preferably fluorine or chlorine. The $C_2$-$C_7$ acyloxy group may be, for example, acetoxy, propionyloxy, n-butyryloxy, isobutyryloxy, n-valeryloxy, iso-valeryloxy, caproyloxy, enanthyloxy or benzoyloxy. The $C_1$-$C_4$ alkyl group which may be substituted by a halogen atom, may be, for example, methyl, ethyl, n-propyl, iso-propyl, n-butyl, chloromethyl, dichloromethyl or trifluoromethyl. The $C_1$-$C_4$ alkoxy group which may be substituted by a halogen atom, may be, for example, methoxy, ethoxy, n-propoxy, iso-propoxy, n-butoxy, chloromethoxy, dichloromethoxy or trifluoromethoxy. The $C_2$-$C_7$ alkocarboxyl group may be, for example, methoxycarbonyl, ethoxycarbonyl, butoxycarbonyl or hexyloxycarbonyl. The $C_1$-$C_{10}$ alkyl or aryl group may be, for example, methyl, ethyl, n-propyl, iso-propyl, n-butyl, phenyl, p-tolyl, o-tolyl, m-tolyl, 1-naphthyl or 2-naphthyl. The number of substituents may be from 1 to 3 substituents of the above type, preferably one such substituent.

The $C_6$-$C_{12}$ aralkyl group containing a condensed aromatic ring or an aromatic heterocyclic ring for $R^1$, may be, for example, 3-pyridylmethyl, 4-pyridylmethyl, benzyl, 1-(3-pyridyl)ethyl, 2-(3-pyridyl)ethyl, 1-(4-pyridyl)ethyl, 2-(4-pyridyl)ethyl, 1-phenyethyl, 2-phenylthyl, 4-phenylbutyl, 8-(1-imidazolyl)octyl, 1-(2naphthyl)ethyl or 2-(1-naphthyl)ethyl.

The one equivalent of a cation for $R^1$ may be, for example, an alkali metal cation such as $Na^+$ or $K^+$, a bivalent or trivalent metal cation such as $\frac{1}{2}Ca^{2+}$, $\frac{1}{2}Zn^{2+}$, $\frac{1}{2}Mg^{2+}$ or $\frac{1}{3}Al^{3+}$, or an ammonium cation such as an ammonium ion or a tetramethylammonium ion.

The $C_3$-$C_{10}$ straight or branched alkyl group for $R^2$ may be, for example, n-propyl, n-butyl, n-pentyl, 1-methylphenyl, 2-methylpentyl, 1,2-dimethylpentyl, n-hexyl, 1-methylhexyl, 2-methylhexyl, 1,2-dimethylhexyl, n-heptyl, n-oxtyl, n-nonyl or n-decyl, and it is preferably n-pentyl, 1-methylpentyl, 2-methylpentyl, 1,2-dimethylpentyl, n-hexyl, 1-methylhexyl or 2-methylhexyl. The alkyl group for the $C_1$-$C_3$ alkyl group substituted by an aryloxy group which may be substituted, may be a straight or branched chain and may be, for example, methyl, n-propyl or iso-propyl. The $C_3$-$C_{12}$ straight or branched alkenyl group for $R^2$ may be, for example, allyl, 3-butenyl, 2-butenyl, 3-methyl-2-butenyl, 4-pentenyl, 3-pentenyl, 4-methyl-3-pentenyl, 2-pentenyl, 5-hexenyl, 4-hexenyl, 3-methyl-4-hexenyl, 5-methyl-2-hexenyl, 2,5-dimethyl-3-hexenyl, 6-heptenyl, 5-heptenyl, 2-ethyl-5-heptenyl, 2,6-dimethyl-5-heptenyl, 7-octenyl, 8-nonenyl, 9-decenyl, 10-undecenyl or 11-dodecenyl, and it is preferably 3-pentenyl or 2,6-dimethyl-5-heptenyl. The $C_3$-$C_8$ straight or branched chain alkynyl group for $R^2$ may be, for example, propargyl, 1-methyl-3-pentynyl, 1,1-dimethyl-3-pentynyl, 1-methyl-3-hexynyl or 1,1-dimethyl-3-hexynyl, and it is preferably 1-methyl-3-hexynyl, 1,1-dimethyl-3-hexynyl or 2-methyl-3-hexynyl. The alkyl group for the substituted $C_1$-$C_3$ alkyl group for $R^2$ may be a straight or branched chain and may be, for example, methyl, ethyl, n-propyl or isopropyl. Such alkyl group is substituted by e.g. a phenyl group, a phenoxy group, a $C_1$-$C_6$ alkoxygroup such as methoxy, ethoxy, n-propoxy or n-butoxy, or a $C_5$-$C_8$ cycloalkyl group such as cyclopentyl or cyclohexyl. $R^2$ is particularly preferably n-pentyl, 2-methylpentyl, 1,1-dimethylpentyl, 2,6-dimethyl-5-heptenyl, 1-methyl-3-pentynyl, 1-methyl-3-hexynyl, 1,1-dimethyl-3-hexynyl, cyclopentylmethyl, cyclohexylmethyl, phenoxymethyl, 1 phenoxyethyl, 1-methyl-1-phenoxyethyl, 2-(3-methoxyphenoxy)ethyl or 2-(4-methoxyphenoxy)ethyl.

$R^3$ is a hydrogen atom, a methyl group or a vinyl group.

Synthesis

Cis-bicyclo[4.3.0]non-2-ene derivatives of the above formulas (I) and (II) of the present invention wherein A is $-CH=CH-CH_2-$, can be produced in accordance with the following reaction schemes.

In the present invention, each of R and $R^4$ in the following formulas is a protecting group for a hydroxyl group. R may be, for example, a 2-tetrahydropyranyl group, a 2-tetrahydrofuranyl group, a methoxymethyl group or a 1-ethoxyethyl group. $R^4$ may be, for example, a tert-butyldimethylsilyl group, a triethylsilyl group, a tribenzylsilyl group or a diphenyl-tert-butyl group. Further, X in the following formulas represents a fluorine atom, a chlorine atom, a bromine atom or an iodine atom.

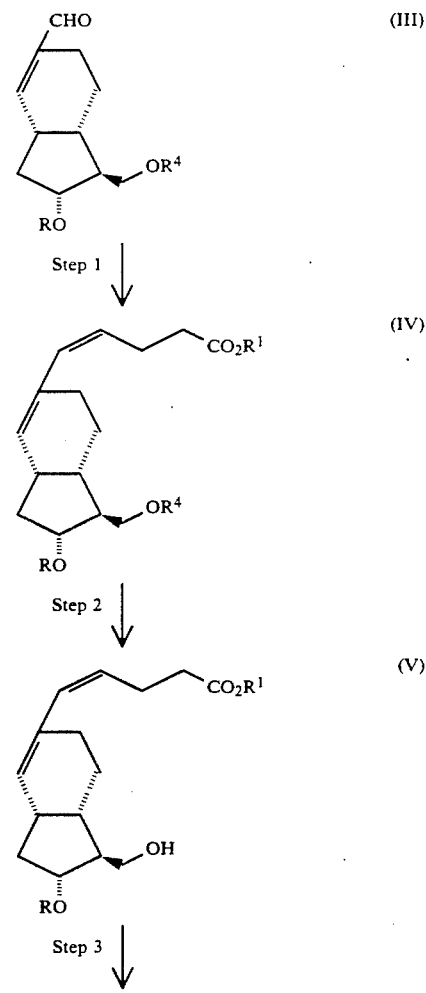

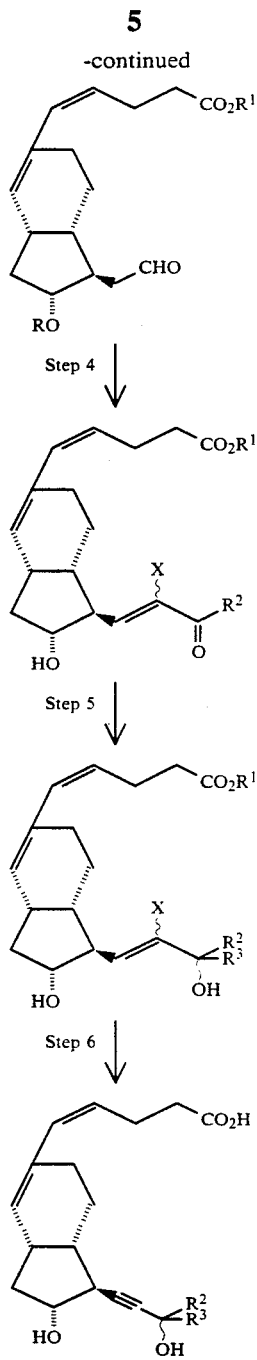

Step 1

This step is to produce a cis-conjugated diene of the above formula (IV) stereoselectively from an enal of the above formula (III) (synthesized in accordance with the lecture number 3j-11-3 on page 381 of the collection of Summaries of Lectures at The 106the Annual Meeting of Japan Pharmaceutical Association in 1986 in Chiba).

In this reaction, an ylide compound prepared from a Wittig reagent obtainable by the reaction of ethyl 4-bromobutyrate with triphenyl phosphine and potassium tert-butoxide can be used. As the solvent for reaction, an ether type solvent such as tetrahydrofuran can be used. The reaction temperature is selected within a range of from $-78°$ C. to room temperature.

Step 2

This step is to produce a primary alcohol of the above formula (V) by selectively removing the protecting group of the primary hydroxyl group of the cis-conjugated diene of the above formula (IV) obtained in Step 1. the reaction for removing the protecting group can be conducted by tetra-n-butylammonium fluoride in tetrahydrofuran.

Step 3

This step is to produce an aldehyde of the above formula (VI) by subjecting the primary alcohol of the above formula (V) obtained in Step 2 to an oxidation reaction. The oxidation reaction can be conducted in a halogenated hydrocarbon such as methylene chloride by means of a Colin's reagent or in a dimethylsulfoxide by means of a sulfur trioxide-pyridine complex.

Step 4

This step is to produce an $\alpha$-haloenone of the above formula (II') by condensing the aldehyde of the above formula (IV) obtained in Step 3 with aluminum enolate obtained by reacting a dihalocarbonyl compound with a dialkylaluminum halide in the presence of zinc powder, and subjecting the alcohol thereby obtained to a sulfonylation reaction or an acetylation reaction without purification, followed by treatment with a base and removing the protecting group for a hydroxyl group. As the dihalocarbonyl compound, an $\alpha$-dibromoketone such as 1,1-dibromo-2-(trans-4-phenylcyclohexyl)ethan-2-one or 1,1-dibromo-2-(4-bipheny)ethan-2-one, or an $\alpha$-bromo-$\alpha$-chloroketone such as 1-bromo-1-chloro-3,3-dimethyl-5-octyn-2-one may, for example, be used. This condensation reaction is conducted in a solvent. As the solvent, an ether type solvent such as tetrahydrofuran or diethyl ether may be used. As the dialkylaluminum halide to be used, dimethylaluminum chloride or diethylaluminum chloride is preferred. The reaction temperature may be selected within a range of from $-50°$ C. to room temperature. The sulfonylation reaction or the acetylation reaction is usually conducted in a solvent, and it is possible to employ a halogenated hydrocarbon solvent such as methylene chloride or chloroform, or a solvent like pyridine. As the reactant, a substituted sulfonyl chloride such as methane sulfonyl chloride or p-toluene sulfonyl chloride, or acetic anhydride may be used. When the reaction is conducted in a halogenated hydrocarbon solvent, the reaction is conducted in the presence of triethylamine as the base. The reaction temperature may be selected within a range of from $-78°$ C. to $-15°$ C.

In this step, the product thus obtained by the sulfonylation reaction or the acetylation reaction is treated at a temperature of from $-10°$ C. to room temperature without isolation in the presence of triethylamine or pyridine or 1,8-diazabicyclo[5.4.0]-7-undecene (hereinafter referred to as DBU). As the solvent for reaction, it is possible to employ a halogenated hydrocarbon solvent such as methylene chloride or chloroform, or a solvent like pyridine.

The reaction conditions for removing a protecting group vary depending upon the type of R in the formula (VI). For example, in the case of a tetrahydropyranyl group, the reaction can be conducted under a weakly acidic condition. For example, the reaction can be conducted using acetic acid-tetrahydrofuran-water or p-toluene sulfonic acid in a catalytic amount in methanol.

The reaction temperature can be selected within a range of from 20° C. to 80° C.

Step 5

This step is to produce an alcohol of the above formula (I') by subjecting the α-haloenone of the above formula (II') obtained in Step 4 to a reduction reaction. For the reduction reaction, sodium borohydride or a reducing agent prepared from 2,6-di-tert-butyl-4-methylphenol and aluminum diisobutyl hydride can be used. the reaction temperature is usually within a range of from −78° to 50° C. The solvent to be used varies depending upon the type of the reducing agent. When sodium borohydride is employed, an alcohol solvent such as methanol or ethanol may be used, and when a reducing agent prepared from 2,6-di-tert-butyl-4-methylphenol and aluminum diisobutyl hydride is employed, toluene or the like may be used.

Two types of stereoisomers formed here, i.e. α-epimer and β-epimer, can readily be separated by silica gel column chromatography.

Step 6

This step is to produce a desired prostacyclin analogues of the above formula (VII) by subjecting the alcohol of the above formula (I') of the present invention to a dehydrohalogenation reaction and an ester hydrolytic reaction. This reaction can be conducted using a double phase solvent of ether-toluene-water by means of an alkali such as sodium hydroxide or potassium hydroxide in the presence of a phase transfer catalyst such as tetra-n-butylammonium hydrogensulfate. The reaction temperature may be selected within a range of from room temperature to 80° C.

This compound may be purified by silica gel column chromatography, or may be converted to a methyl ester by using an ether solution of diazomethane in an ethyl ether or in a solvent mixture of ethyl ether-methanol, then purified by silica gel column chromatography and again subjected to ester hydrolysis.

The cis-bicyclo[4.3.0]nona-2-ene derivatives of the formulas (I) and (II) of the present invention wherein A is —CH$_2$—CH$_2$—O—, can be produced in accordance with the following reaction schemes.

In the present invention, R in the following formulas is a protecting group for a hydroxyl group, and as such protecting group, a 2-tetrahydropyranyl group, a 2-tetrahydrofuranyl group, a methoxymethyl group or a 1-ethoxyethyl group may, for example, be mentioned. Further, X in the following formulas represents a fluorine atom, chlorine atom, a bromine atom or an iodine atom.

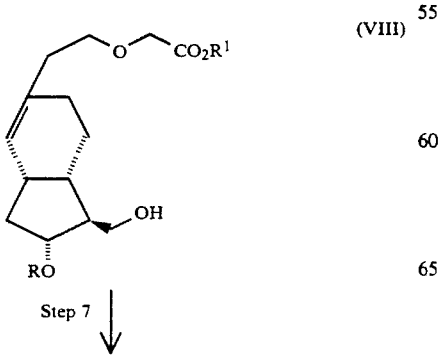

(VIII)

Step 7 ↓

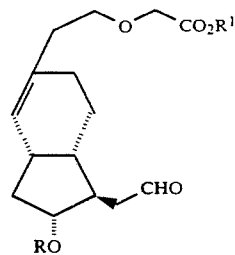

(IX)

Step 8 ↓

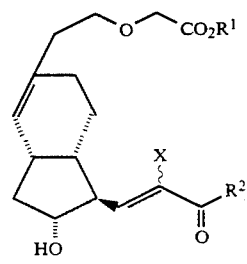

(II'')

Step 9 ↓

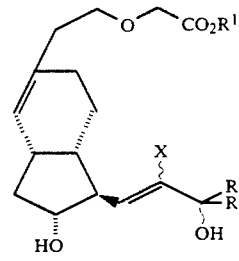

(I'')

Step 10 ↓

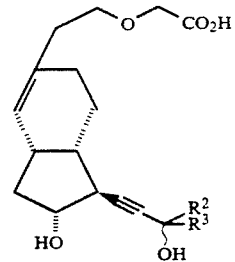

(X)

Step 7

This step is to produce an aldehyde of the above formula (IX) by subjecting a primary alcohol of the above formula (XIII) to the same operation as the above Step 3.

Step 8

This step is to produce an α-haloenone of the above formula (II') by subjecting the aldehyde of the above formula (IX) obtained in the above Step 7 to the same operation as in the above Step 4.

Step 9 This step is to produce an alcohol of the above formula (I") by subjecting the α-haloenone of the above formula (II") obtained in the above Step 7 to the same operation as in the above Step 5.

Two types of stereoisomers produced here, i.e. α-epimer and β-epimer, can readily be separated by silica gel column chromatography.

Step 10

This step is to produce a prostacyclin analogues of the above formula (X) by subjecting the alcohol of the above formula (I") obtained in the above Step 9 to the same operation as in the above Step 6.

The present inventors have studied in detail the the pharmacological activities of the prostacyclin analogues of the above formulas (VII) and (X) prepared from the cis-bicyclo[4.3.0]non-2-ene derivatives (I) and (II) of the present invention As a result, it has been found that as compared with $PGI^2$, they have equal or a few times greater blood platelet anti-aggregatory activities, and they have remarkable cytoprotective activities by oral administration against ethanol ulcer using animals, and further they are excellent in the stability, for example, they are stable even in an acidic solution. The present invention has been accomplished on the basis of this discovery.

The compounds of the formulas (VII) and (X) prepared from the compounds of the present invention can be administered orally or non-orally for the treatment.

The drugs for oral administration may be solid formulations such as powders, granules, capsules, tablets or liquid formulations such as syrups or elixirs. The drug for non-oral administration may be injection drugs, rectal administration drugs, skin application drugs or inhalation drugs. These drugs can be prepared in accordance with a conventional method by mixing such an active ingredient with a pharmaceutically acceptable additives or adjuvant. Further, it may be made in the form of a long-lasting agent in accordance with a known technique.

For the preparation of solid formulations for oral administration, the active ingredient may be mixed with an additive such as lactose, starch, crystalline cellulose, calcium lactate, magnesium metasilicate aluminate or silicic anhydride to obtain a powder, or if necessary, a binder such as sucrose, hydroxypropyl cellulose or polyvinylpyrrolidone and a disintegrator such as carboxymethyl cellulose or calcium carboxylmethyl cellulose, may be added, and the mixture is subjected to wet or dry granulation to obtain granules. For the preparation of tablets, these powders or granules may be tabletted by themselves or after an addition of a lubricant such as magnesium stearate or talc. These granules or tablets may be formed into enteric coating formulations by coating them with an enteric coating agent such as hydroxypropylmethyl cellulose stearate, methyacrylic acid or a methyl methacrylate copolymer, or may be formulated into long-lasting formulations by coating them with ethyl cellulose, carnauba wax, hardened oil, etc.

For the preparation of capsules, the powders or granules, may be filled in hard capsules, or active ingredients may be dissolved in glycerol, polyethylene glycol, sesame oil, olive oil or the like, and then coated with a gelatin film to obtain soft capsules.

For the preparation of liquid formulations for oral administration, an active ingredient and a sweetening agent such as sorbitol or glycerol, may be dissolved in water to obtain a clear syrup, or refined oil or ethanol may be added thereto to obtain an elixir, or gum arabic or tragant, polysolvate 80 or sodium carboxyl methyl cellulose, may be added thereto to obtain an emulsion or suspension. If desired, additives such as corrigents, coloring agents or storage agents may be added to there liquid formulation.

For the preparation of an injection solution, an active component may be dissolved in distilled water for injection, if necessary, together with a pH controlling agent such as hydrochloric acid, sodium hydroxide, lactic acid, sodium lactate, sodium hydrogenphosphate or sodium dihydrogenphosphate, and an isotonic agent such as sodium chloride or glucose, then septically filtered and filled in an ample, or mannitol, dextrin, cyclodextrin, gelatin or the like may be added thereto, followed by freeze drying under vacuum, to obtain an injection drug of the type which is to be dissolved at the time of the injection. Further, it is possible to prepare an emulsion for injection by emulsifying an active ingredient in water by an addition of lecitin, polysolvate 80 or polyoxyethylene hardened caster oil.

For the preparation of a rectal administration drug, an active ingredient and a suppository material such as cacao butter fatty acid tri-, di- or mono glyceride or polyethylene glycol, or an active ingredient may be dissolved in polyethylene glycol, soybean oil or the like, followed by coating with a gelatin film.

For the preparation of a skin application drug, an active ingredient may be added to white vaseline, beeswax, liquid paraffin, polyethylene glycol or the like, and the mixture is kneaded, if necessary under heating, to obtain an ointment, or it may be kneaded with an adhesive agent such as rosin or an alkyl acrylate polymer, and the mixture is then spread on a non-woven fabric of polyethylene, etc. to obtain a tape drug.

For the preparation of an inhalation drug, an active ingredient is dissolved or dispersed in a propellant such as Freon gas and filled in pressure resistant container to obtain an aerosol.

The dose of the prostacyclin analogues prepared from the compounds of the present invention varies depending upon the age, the weight and the diseased state of the patient, but is usually within a range of from 1 μg to 500 mg per day, and may be administered at once or in several times.

Now, the present invention will be described in further detail with reference to Reference Examples, Synthesis Examples, Test Examples and Formulation Examples. However, it should be understood that the present invention is by no means restricted to these specific Examples.

REFERENCE EXAMPLE 1

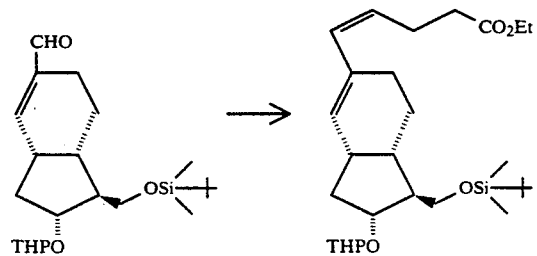

Under an argon atmosphere, (3-carboethoxypropyl)-triphenylphosphonium bromide (1.45 g, 3.17 mmol) was suspended in 8 ml of tetrahydrofuran (hereinafter referred to as THF), and 12 ml of a THF solution of potassium tert-butoxide (356 mg, 3.17 mmol) was dropwise added thereto at room temperature. The mixture was stirred for 15 minutes. Then, 5 ml of a THF solution of 3-formyl-7-exo-tert-butyldimethylsilyloxymethyl-8-endo-tetrahydropyranyloxy-cis-bicyclo[4.3.0]non-2-ene (500 mg, 1.27 mmol) was dropwise added thereto at −78° C., and the mixture was stirred for 4 hours. Then, the temperature was raised to room temperature, and the mixture was stirred for one hour. Then, 20 ml of a saturated ammonium chloride aqueous solution was added thereto, and the mixture was extracted with ethyl ether. The crude product thereby obtained was purified by silica gel column chromatography (n-hexane : ethyl ether=1 : 5) to obtain 621 mg (99.0%) of 3-(4-ethoxycarbonyl-cis-1-butenyl)-7-exo-tert-butyldimethylsilyloxy-8-endo-tetrahydropyranyloxy-cisbicyclo[4.3.0]non-2-ene as a colorless oily substance.

IRγmax(neat): 2950, 2930, 2860, 1730, 1030, 835 cm⁻¹.

NMR(CDCl₃)δ: 0.05 (6H, s), 0.89 (9H,s), 1.25 (3H, t, J=7.5Hz), 4.61 (1H, bs), 5.00 5.30 (1H, m), 5.58 (1H, bs), 5.79 (1H,d, J=12.5Hz).

REFERENCE EXAMPLE 2

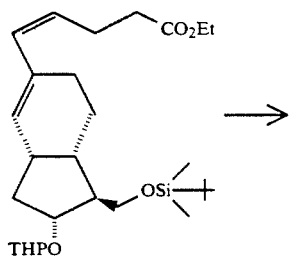

3-(4 ethoxycarbonyl cis-1-butenyl)-7-exo-tert-butyldimethylsilyloxymethyl-8-endo-tetrahydropyranyloxy-cis-bicyclo[4.3.0]non-2-ene (656 mg, 1.33 mmol) was dissolved in THF (6 ml), and tetra-n-butylammonium fluoride (3.03 ml, 1.1 M THF solution, 3.33 mmol) was dropwise added under cooling with ice. The mixture was stirred at room temperature for 17 hours. Then, 20 ml of a saturated sodium chloride aqueous solution was added, and the mixture was extracted with ethyl ether. The extract was dried over anhydrous magnesium sulfate. Then, the solvent was distilled off under reduced pressure, and the crude product thereby obtained was purified by silica gel column chromatography (n-hexane : ethyl ether=2 : 1) to obtain 440 mg (87.0%) of 3-(4-ethoxycarbonyl-cis-1-butenyl)-7-exo-hydroxymethyl-8-endo-tetrahydropyranyloxy-cis-bicyclo[4.3.0]non-2-ene as a slightly yellow oily substance.

IRγmax(neat): 3450, 2950, 2870, 1735 cm⁻¹.

NMR(CDCl₃): 1.25 (3H, t, J=7.5Hz), 4.13 (2H, q, J=7.5 Hz), 5.05-5.41 (1H, m), 5.58 (1H, bs), 5.80 (1H, d, J=12.5Hz).

REFERENCE EXAMPLE 3

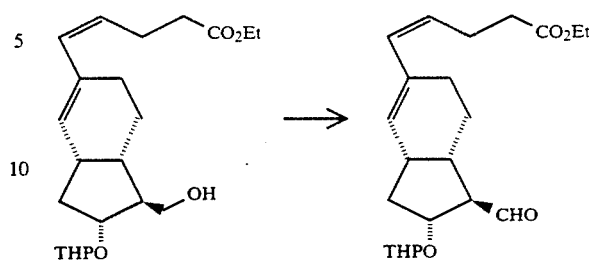

Under an argon atmosphere, 3-(4-ethoxycarbonyl-cis-1 butenyl)-7-exo-hydroxymethyl-8-endo-tetrahydropranyloxy-cis-bicylco[4.3.0]non-2-ene (200 mg, 0.529 mmol) was dissolved in dimethyl sulfoxide (2 ml). Triethylamine (0.44 ml, 3.17 mmol) and a dimethyl sulfoxide solution (2 ml) of sulfur trioxide-pyridine complex (505 mg, 3.17 mmol) was added thereto, and the mixture was stirred at room temperature for 15 minutes. Then, ice water was added, and the mixture was extracted with ethyl acetate. The extract was washed with water and a saturated sodium chloride aqueous solution and then dried over anhydrous magnesium sulfate. Then, the solvent was distilled off to obtain 3-(4-ethoxycarbonyl-cis-1-butenyl)-7-exo-formyl-8-endo-tetrahydropyranyloxy-cis-bicyclo[4.3.0]non-2-ene, which was used for the next reaction without purification.

EXAMPLE 1

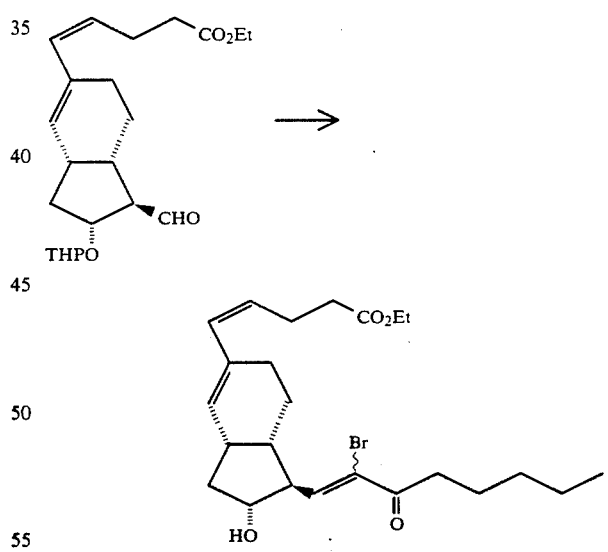

Zinc powder (69 mg, 1.06 mmol) and cuprous bromide (catalytic amount) were suspended in THF (4 ml), and diethylaluminum chloride (1.44M hexane solution, 0.74 ml, 1.06 mmol) was dropwise added thereto at room temperature. The mixture was stirred for 35 minutes. The reaction solution was cooled to −5° C., and a THF solution (5 ml) of 3-(4-ethoxycarbonyl-cis-1-butenyl)-7-exo-formyl-8-endo-tetrahydropyranyloxy-cisbicyclo[4.3.0]non-2-ene (200 mg, 0.53 mmol) and 1,1-dibromoheptan-2-one (576 mg, 2.12 mmol) was dropwise added thereto over a period of 10 minutes. Then, the mixture was stirred at the same temperature for 60 minutes. To the reaction solution, a saturated potassium hydrogencarbonate aqueous solution was added, and the mixture was extracted with ethyl ether. The ether layer was washed with a saturated sodium chloride aqueous solution and then dried over anhydrous magnesium sulfate. Then, the solvent was distilled off, and the residue thereby obtained was dissolved in methylene chloride (7 ml). Then, triethylamine (2.20 ml) was added thereto at −40° C., and then methanesulfonylchloride (0.61 ml) was dropwise added thereto. Further, 1,8-diazabicyclo[5.4.0]-7-undecene (0.79 ml) was dropwise added thereto at 0° C., and the mixture was stirred at the same temperature for 12 hours. To the reaction solution, ice water was added, and the mixture was extracted with ethyl ether. The ether layer was washed with water and a saturated sodium chloride aqueous solution, and then dried over anhydrous magnesium sulfate. Then, the solvent was distilled off, and the residue thereby obtained was purified by silica gel chromatography (ethyl ether : n-hexane=1:6) to obtain 3-(4-ethoxycarbonyl-cis-1-butenyl)-7-exo-(2-bromo-3-oxo-1-octenyl)-8-endo-tetrahydropyranyloxy-cis-bicyclo[4.3.0]non-2-ene (192 mg, 66%) as a colorless oily substance. To a THF solution (3 ml) of this compound (190 mg, 0.35 mmol), a 65% acetic acid aqueous solution (3 ml) was added, and the mixture was stirred at 60° C. for 6 hours. To the reaction solution, a saturated sodium hydrogencarbonate aqueous solution was added to adjust the pH to 8. Then, the mixture was extracted with ethyl acetate, and the extract was washed with a saturated sodium chloride aqueous solution and then dried over anhydrous magnesium sulfate. Then, the solvent was distilled off, and the residue thereby obtained was purified by silica gel column chromatography (n-hexane : ethyl ether=1 : 1) to obtain 3-(4-ethoxycarbonyl-cis-1-butenyl)-7-exo-(2-bromo-3-oxo-1-octenyl)-8-endo-hydroxy-cis-bicyclo[4.3.0]none-2-ene (130 mg, 80%) as a colorless oily substance.

IRγmax(neat): 3450, 2950, 1730, 1690, 1610, 1450 cm⁻¹.

NMR(CDCl₃)δ: 0.88 (3H, t, J=6.8Hz), 1.24 (3H, t, J=8.0Hz), 4.10 (1H, q, J=6.4Hz), 5.28 (1H, m), 5.54 (1H, bs), 5.82 (1H, d, J=12.0Hz), 7.00 (1H, d, J=9.2Hz).

EXAMPLE 2 to 4

In Table 1, the IR and NMR spectram data of the compounds prepared in the same manner as in Example 1 are presented.

TABLE 1

| Example No. | R⁵ | Yield (%) a) | IR$\nu_{max}$ (neat)cm⁻¹ | NMR (CDCl₃)δ |
|---|---|---|---|---|
| 2 | Me, H (propargyl group) | 44 | 3450, 2950, 1730, 1690, 1610, 1450. | 1.10(3H, t, J=7.8Hz), 1.4(3H, d, J=6.0Hz), 1.16 (3H, t, J=8.0Hz), 4.14(2H, q, J=8.0Hz), 5.34(1H, m), 5.60(1H, bs), 5.96(1H, d, J=12.0Hz), 7.08(1H, d, J=10.0Hz). |
| 3 | Me, Me (propargyl group) | 43 | 3450, 2950, 1730, 1690, 1610. | 1.10(3H, t, J=7.2Hz), 1.18(3H, t, J=8.0Hz), 1.40 (6H, s), 4.13(2H, q, J=8.0Hz), 4.68(1H, m), 5.60 (1H, bs), 5.85(1H, d, J=12.0Hz), 6.40(1H, d, J= 9.5Hz) |
| 4 | (alkenyl group) | 53 | 3450, 2940, 1730, 1680, 1610, 1440. | 0.94(3H, d, J=7.2Hz), 1.24(3H, t, J=8.0Hz), 1.60 (3H, s), 1.68(3H, s), 4.10(2H, q, J=8.0Hz), 5.08(1H, m), 5.30(1H, m), 5.54(1H, bs), 5.94(1H, d, J=12.0Hz), 6.98(1H, d, J=9.0Hz). | a) Yield from the aldehyde

EXAMPLE 5

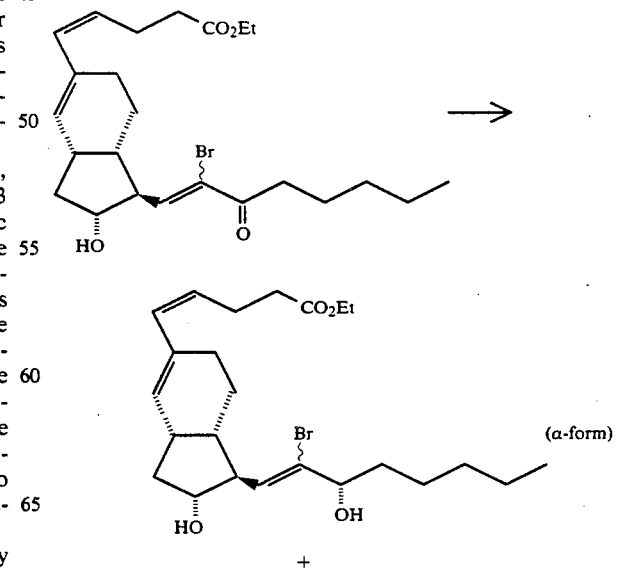

-continued

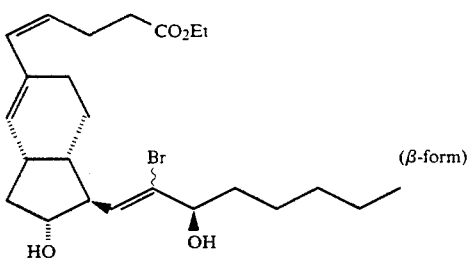
(β-form)

spectrum data of the α-epimer are shown below. The spectrum data of the β-epimer were the same.

IRγmax(neat): 3400, 2900, 1730, 1640, 1440 cm$^{-1}$.

NMR(CDCl$_3$)δ: 0.88 (3H, t, J=7.0Hz), 1.24 (3H, t, J=8.0Hz), 4.00 (1H, m), 4.15 (2H, q, J=8.0Hz), 5.28 (1H, m), 5.52 (1H, bs), 5.80 (1H, d, J=12.0 Hz), 5.88 (1H, d, J=9.2 Hz).

EXAMPLES 6 to 8

In Table 2, the IR and NMR spectrum data of α-epimer forms of the compounds prepared in the same manner as in Example 5 are presented. The spectrum data of the β-epimer forms were the same.

TABLE 2

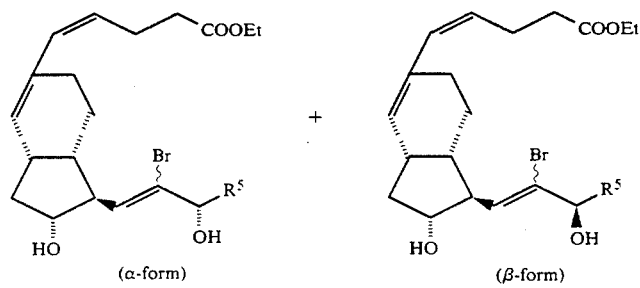

| Example No. | R$^5$ | Yield (%) a) | IRν$_{max}$ (neat)cm$^{-1}$ | NMR (CDCl$_3$)δ |
|---|---|---|---|---|
| 6 | Me⋯⋯H (propargyl with Me) | α: 76 β: 11 | 3400, 2950, 1730, 1650, 1450. | 1.00(3H, d, J=6.0Hz), 1.18(3H, t, J=7.8Hz), 1.28 (3H, t, J=8.0Hz), 4.00(1H, bt, J=6.0Hz), 4.18(2H, q, J=8.0Hz), 5.30(1H, m), 5.60(1H, bs), 5.85(1H, d, J=12.0Hz), 5.95(1H, d, J=11.2Hz). |
| 7 | Me⋯⋯Me (propargyl with dimethyl) | α: 72 β: 17 | 3450, 2950, 1730. | 1.06(3H, s), 1.08(3H, s), 1.18(3H, t, J=8.0Hz), 1.25 (3H, t, J=8.0Hz), 4.14(2H, q, J=8.0Hz), 5.30(1H, m), 5.54(1H, bs), 5.90(1H, t, J=12.0Hz), 5.94(1H, d, J=10.0Hz). |
| 8 | (trisubstituted alkenyl chain) | α: 70 β: 20 | 3450, 2950, 1740, 1650, 1440. | 0.94(3H, d, J=7.2Hz), 1.24(3H, d, J=8.0Hz), 1.60 (3H, s), 1.68(3H, s), 4.00(2H, m), 4.10(2H, q, J=8.0Hz), 5.08(1H, m), 5.34(1H, m), 5.50(1H, bs), 5.80(1H, d, J=12.0Hz), 5.98(1H, d, J=8.8Hz). |

To a toluene solution (4-ml) of 2,6-di-tert-butyl-4-methylphenol (803 mg, 3.65 mmol), diisobutylaluminum hydride (1M toluene solution, 2.7 ml, 2.7 mmol) was gradually added under an argon atmosphere at from −10° C. to −15° C., and the mixture was stirred at the same temperature for one hour. Then, at −78° C., a toluene solution (6 ml) of 3-(4-ethoxycarbonyl-cis-1-butenyl)-7-exo-(2-bromo-3-oxo-1-octenyl)-8-endo-hydroxy-cis-bicyclo[4.3.0]non-2-ene (125 mg, 0.27 mmol) was dropwise added thereto, and the mixture was stirred at −78° C. for 40 minutes. Then, the temperature was raised from −78° C. to −20° C. over a period of 3 hours. To the reaction solution, a saturated sodium chloride aqueous solution was added, and the mixture was extracted with ethyl acetate. The organic layer was washed with water and a saturated sodium chloride aqueous solution and dried over anhydrous magnesium sulfate. Then, the solvent was distilled off, and the residue thereby obtained was purified by silica gel column chromatography (n-hexane : ethyl ether=1 : 5) to obtain 3-(4-ethoxycarbony-cis-1-butenyl)-7-exo-(3α-hydroxy-2-bromo-1-octenyl)-8-endo-hydroxy-cis-bicyclo[4.3.0]non-2-ene (78 mg, 70%) as a highly polar component and 3-(4-ethoxycarbonyl-cis-1-butenyl)-7-exo-(3β-hydroxy-2-bromo-1-octenyl)-8-endo-hydroxy-cis-bicyclo[4.3.0]non-2-ene (21 mg, 17%) as a low polar component, each as a colorless oily substance. The

REFERENCE EXAMPLE 4

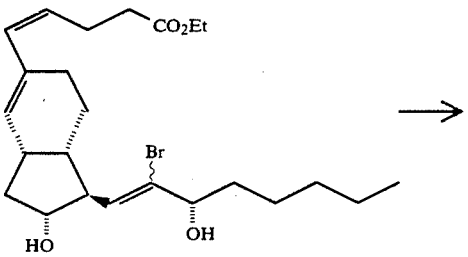

→

REFERENCE EXAMPLES 5 TO 7

In Table 3, the IR and NMR spectrum data of the compounds prepared in the same manner as in Reference Example 4 are presented.

TABLE 3

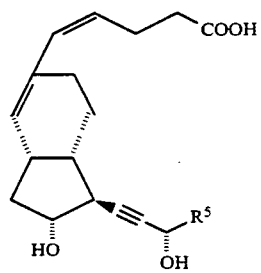

| Reference Example No. | $R^5$ | Yield (%) | IR$\nu_{max}$ (neat)cm$^{-1}$ | NMR (CDCl$_3$)$\delta$ |
|---|---|---|---|---|
| 5 (b) | Me,,,H ≡ (propargyl with Me,H) | 72.5 | 3400, 2950, 2220, 1700, 1420. | 1.07(1H, d, J=6.2Hz), 1.10(1H, t, J=8.0Hz), 4.10 (2H, q, J=6.0Hz), 4.40(1H, dd, J=1.5, 3.0Hz), 4.80 (2H, m), 5.28(1H, m), 5.46(1H, bs), 5.78(1H, d, J=12.0Hz). |
| 6 (c) | Me,,,Me ≡ | 87.0 | 3450, 2950, 2200, 1700, 1420. | 1.00(6H, s), 1.10(3H, t, J=7.2Hz), 4.10(3H, m), 4.26 (1H, d, J=2.0Hz), 5.26(1H, m), 5.48(1H, bs), 5.74(1H, d, J=12.0Hz). |
| 7 (d) | (diene with CO$_2$H) | 62.0 | 3400, 2950, 1700, 1440. | 0.94(3H, d, J=7.2Hz), 1.60(3H, s), 1.68(3H, s), 4.10 (2H, q, J=6.0Hz), 4.38(3H, m), 5.04(1H, m), 5.26(1H, m 5.44(1H, bs), 5.74(1H, d, J=12.0Hz). |

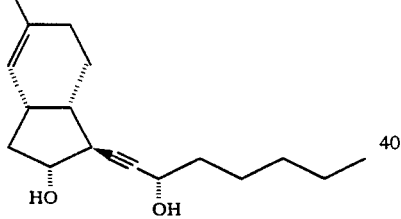

Compound (a)

Tetra-n-butyl ammonium hydrogen sulfate (357 mg, 1.05 mmol) was dissolved in water (0.1 ml). Then, an ethyl ether-toluene solution (3 : 1, 3 ml) of 3-(3-ethoxycarbonyl-cis-1-butenyl)-7-exo-(3α-hydroxy-2-bromo-1-octenyl)-8-endo-hydroxy-cis-bicyclo[4.3.]non-2-ene (98 mg, 0.21 mmol) was added thereto. Then, a 50% sodium hydroxide aqueous solution (1 ml) was gradually dropwise added thereto at 0° C., and the mixture was stirred at 50° C. for 36 hours. To the reaction solution, water was added, and the pH was adjusted to 4 with a 5% hydrochloric acid aqueous solution. Then, the mixture was extracted with ethyl acetate, and the extract was washed with water and a saturated sodium chloride aqueous solution and then, dried over anhydrous magnesium sulfate. Then, the solvent was distilled off to obtain 3-(4-carboxy-cis-1-buteny)-7-exo-(3α-hydroxy-1-octynyl)-8-endo-hydroxy-cis-bicyclo[4.3.0]non-2-ene (compound (A) 49.8 mg, 66.0%) as a colorless oily substance.

IR$\gamma$max(neat) 3450, 2940, 2220, 1710, 1440 cm$^{-1}$.

NMR(CDCl$_3$)$\delta$: 0.88 (3H, t, J=7.0Hz), 4.10 (1H, q, J-6.4Hz 4.36 (1H, m), 4.80 (2H, m), 5.24 (1H, m), 5.46 (1H, bs), 5.78 (1H, d, J=12.0Hz).

REFERENCE EXAMPLE 8

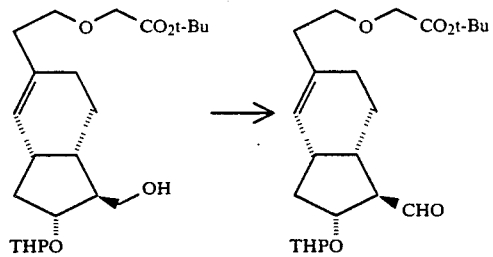

Under an argon atmosphere, 3-(3-oxa-4-tert-butoxycarbonylbutyl)-7-exo-hydroxymethyl-8-endo-tetrahydropyranyloxy-cis-bicyclo[4.3.0]-non-2-ene (200 mg, 0.488 mmol) was dissolved in dimethyl sulfoxide (2 ml). Triethylamine (0.41 ml; 2.93 mmol) and a dimethyl sulfoxide solution (2 ml) of sulfur trioxide-pyridine complex (466 mg, 2.93 mmol) was added thereto, and the mixture was stirred at room temperature for 15 minutes. Then, ice water was added to the reaction solution, and the mixture was extracted with ethyl acetate. The extract was washed with water and a saturated sodium chloride aqueous solution and then dried over anhydrous magnesium sulfate. Then, the solvent was distilled off to obtain 3-(3-oxa-4-tert-butoxycarbonylbutyl)-7-exo-formyl-8-endo-tetrahydropyranyloxy-cis-bicyclo[4.3.0]non-2-ene, which was used for the next reaction without purification.

EXAMPLE 9 1

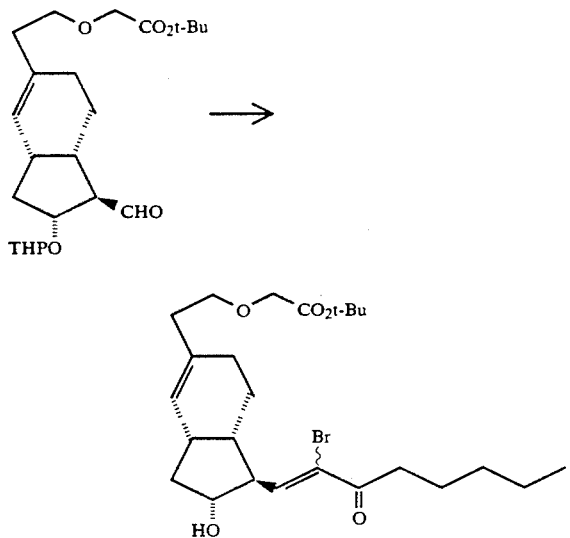

Zinc powder (64 mg, 0.98 mmol) and cuprous bromide (catalytic amount) were suspended in THF (4 ml), and diethylaluminum chloride (1.44M hexane solution, 0.68 ml, 0.98 mmol) was dropwise added thereto at room temperature. The mixture was stirred for 30 minutes. The reaction solution was cooled to −5° C., and a THF solution (5 ml) of 3-(3-oxa-4-tert-butoxycarbonyl-butyl)-7-exo-formyl-8-endo-tetrahydropyranyloxy-cis-bicyclo[4.3.0]non-2-ene (200 mg, 0.49 mmol) and 1,1-dibromoheptan-2-one (468 mg, 1.72 mmol was dropwise added thereto over a period of 10 minutes. Then, the mixture was stirred at the same temperature for 40 minutes. To the reaction solution, a saturated potassium hydrogencarbonate aqueous solution was added, and the mixture was extracted with ethyl ether. The ether layer was washed with a saturated sodium chloride aqueous solution and then dried over anhydrous magnesium sulfate. Then, the solvent was distilled off, and the residue thereby obtained was dissolved in methylene chloride (7 ml). Then, triethylamine (2.20 ml) was added thereto at −40° C., and then methanesulfonyl chloride (0.61 ml) was dropwise added thereto. Further, 1,8-diazabicyclo[5.4.0]-7-undecnene (0.79 ml) was dropwise added at 0° C., and the mixture was stirred at the same temperature for 12 hours. To the reaction solution, ice water was added, and the mixture was extracted with ethyl ether. The ether layer was washed with water and a saturated sodium chloride aqueous solution, and then dried over anhydrous magnesium sulfate. Then, the solvent was distilled off, and the residue thereby obtained was purified by silica gel column chromatography (ethyl ether : n-hexane=1 : 6) to obtain 3-(3-oxa-4-tert-butoxycarbonylbutyl)-7-exo-(2-bromo-3-oxo-1-octenyl)-8-endo-tetrahydropyranyloxy-cisbicy-clo[4.3.0]non-2-ene (168 mg, 59%) as a colorless oily substance. To a THF solution (3 ml) of this compound (165 mg, 0.28 mmol), a 65% acetic acid aqueous solution (3 ml) was added, and the mixture was stirred at 60° C. for 5 hours. To the reaction solution, a saturated sodium hydrogencarbonate aqueous solution was added to adjust the pH to 8. Then, the mixture was extracted with ethyl acetate, and the extract was washed with a saturated sodium chloride aqueous solution and then dried over anhydrous magnesium sulfate. Then, the solvent was distilled off, and the residue thereby obtained was purified by silica gel column chromatography (n-hexane : ethyl ether=1 : 1) to obtain 3-(3-oxa-4-tert-butoxycarbonylbutyl)-7-exo-(2-bromo-3-oxo-1-octenyl)-8-endo-hydroxy-cis-bicyclo[4.3.0]non-2-ene (130 mg, 94%) as i a colorless oily substance.

IRγmax(neat): 3450, 2920, 1740, 1680, 1610, 1450 cm$^{-1}$.

NMR(CDCl$_3$)δ: 0.90 (3H, t, J=7.2Hz), 1.44 (9H, s), 3.62 (2H, t, J=8.0Hz), 3.96 (2H, s), 4.08 (1H, q, J=6.4Hz), 5.44 (1H, bs), 6.98 (1H, d, J =9.5Hz).

EXAMPLES 10 TO 16

In Table 4, the IR and NMR spectrum data of the compounds prepared in the same manner as in Example 9 are presented.

TABLE 4

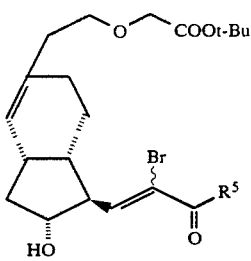

| Example No. | R$^5$ | Yield (%) a) | IR$\nu_{max}$ (neat)cm$^{-1}$ | NMR (CDCl$_3$)δ |
|---|---|---|---|---|
| 10 | Me ̈ H alkynyl | 54 | 3450, 2900, 1740, 1680, 1600, 1440. | 1.08(3H, t, J=7.8Hz), 1.22(3H, d, J=6.0Hz), 1.48 (9H, s), 3.10(1H, m), 3.62(2H, t, J=8.0Hz), 3.95 (2H, s), 4.10(1H, m), 5.44(1H, bs), 6.95(1H, d, J=9.2Hz). |
| 11 | Me ̈ Me alkynyl | 41 | 3500, 2950, 1740, 1690, 1620. | 1.10(3H, t, J=7.2Hz), 1.38(6H, s), 1.50(9H, s), 3.60 (2H, t, J=7.2Hz), 3.95(2H, s), 4.10(1H, m), 5.42(1H, bs), 6.26(1H, d, J=8.8Hz). |
| 12 | (geranyl-type chain) | 46 | 3450, 2900, 1740, 1680, 1610, 1420. | 0.92(3H, d, J=7.2Hz), 1.45(9H, s), 1.60(3H, s), 1.68 (3H, s), 3.60(2H, t, J=7.2Hz), 3.92(2H, s), 4.08(1H, m), 5.06(1H, m), 5.40(1H, bs), 6.90(1H, d, J=9.2Hz). |

TABLE 4-continued

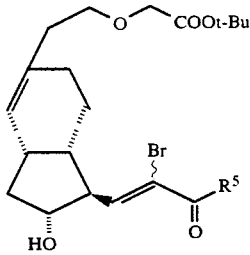

| Example No. | R⁵ | Yield (%) a) | IR$\nu_{max}$ (neat)cm$^{-1}$ | NMR (CDCl$_3$)δ |
|---|---|---|---|---|
| 13 | Me-CH(-)-O-Ph | 39 | 3450, 2950, 1740, 1700, 1600, 1500, 1240. | 1.45(9H, s), 1.65(3H, d, J=7.8Hz), 3.64(2H, t, J= Hz), 3.96(2H, s), 4.16(1H, q, J=6.0Hz), 5.44(1H, bs), 6.84(2H, m), 7.04(1H, d, J=7.5Hz), 7.20(5H, m). |
| 14 | Me,Me-C(-)-O-Ph | 46 | 3400, 2900, 1740, 1600, 1490, 1240. | 1.40(9H, s), 1.64(3H, s), 1.66(3H, s), 2.95(1H, m), 3.54(2H, t, J=7.8Hz), 3.90(2H, s), 5.34(1H, bs), 6.54–7.30(5H, m), 7.62(1H, d, J=10.0Hz). |
| 15 | Me,Me-C(-)-O-C₆H₄-OCH₃ | 58 | 3400, 2950, 1740, 1600, 1490, 1240. | 1.44(9H, s), 1.66(6H, s), 3.60(2H, t, J=8.0Hz), 3.76 (3H, s), 3.96(3H, s), 4.00(1H, m), 5.40(1H, bs), 6.94 (4H, m), 7.40(1H, d, J=9.2Hz). |
| 16 | -CH₂-cyclopentyl | 65 | Used for the next reaction | | a) Yield from the aldehyde

EXAMPLE 17

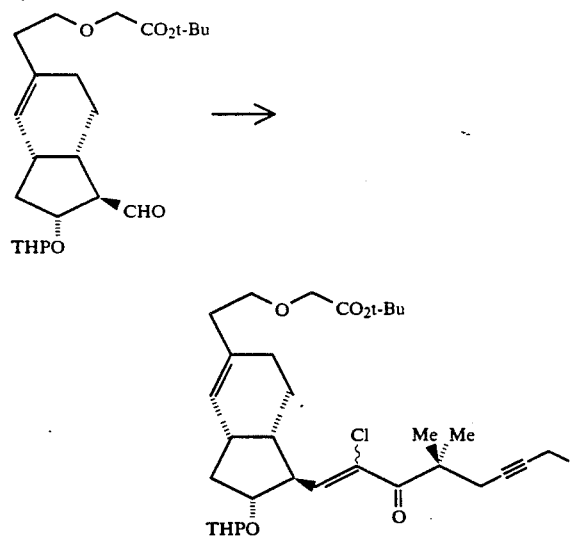

Under an argon atmosphere, zinc powder (287.0 mg, 4.42 mmol) and cuprous bromide (63.0 mg, 0.44 mmol) were suspended in THF (20.0 ml), and diethylaluminum chloride (1.0M hexane solution, 4.20 ml, 4.20 mmol) was dropwise added thereto at room temperature. Then, the mixture was stirred at room temperature. Then, the mixture was stirred at room temperature for 45 minutes. The reaction solution was cooled to −20° C., and a THF solution (25.0 ml) of 3-(3-oxa-4-tert-butoxycarbonylbutyl)-7-exo-formyl-8-endo-tetrahydropyranyloxy-cis-bicyclo[4.3.0]non-2-ene (1.50 g, 3.68 mmol) and 1-bromo-1-chloro-3,3-dimethyl-5-octyn-2-one (2.43 g, 9.20 mmol) was dropwise added thereto over a period of 20 minutes. Then, the mixture was stirred at the same temperature for 35 minutes. To the reaction solution, saturated potassium hydrogencarbonate aqueous solution was added at −20° C., and the mixture was extracted with ethyl ether. The organic layer was washed with water and a saturated sodium chloride aqueous solution and then dried over anhydrous magnesium sulfate. Then, the solvent was distilled off under reduced pressure, and the residue thereby obtained was dissolved in methylene chloride (46.0 ml). Under an argon atmosphere, triethylamine (30.0 ml, 216.8 mmol) was dropwise added to the reaction solution at −40° C. Then, methanesulfonyl chloride (5.12 ml, 66.5 mmol) was dropwise added thereto. The reaction solution was stirred at 0° C. for 30 minutes, and then 1,8-diazabicyclo[5.4.0]-7-undenene (9.93 ml, 66.5 mmol) was dropwise added thereto at the same temperature. The mixture was stirred at 0° C. for 13.5 hours. To the reaction solution, ice water was added, and the mixture was extracted with ethyl ether. The organic layer was washed with water and a saturated sodium chloride aqueous solution, and then dried over anhydrous magnesium sulfate. Then the solvent was distilled off under reduced pressure, and the residue thereby obtained was purified by silica gel column chromatography (ethyl ether : n-hexane=1 : 3) to obtain 3-(3-oxa-4-tert-butoxycarbonylbutyl)-7-exo-(2-chloro- 4,4-dimethyl-3-oxo-1-nonen-6-ynyl)-8-endo-tetrahydroxypyranyloxy-cis-bicyclo[4.3.0]non-2-ene (1.85 g, 85%) as a slightly yellow oily substance.

IRγmax(neat):2926, 1749, 1689, 1610, 1458, 1368, 1254 cm$^{-1}$.

NMR(CDCl$_3$)δ: 1.10 (3H, t, J=7.2Hz), 1.37 (6H, s), 1.48 (9H, s), 2.52 (2H, t, J=2.0Hz), 3.57 (2H, t, J=7.2Hz), 3.93 (2H, s), 4.60 (1H, m), 5.37 (1H, brs), 6.38, 6.41 (total 1H, d and d, each J=9.2Hz).

EXAMPLE 18

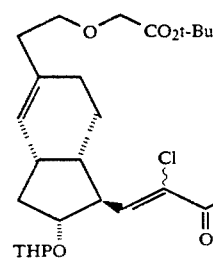

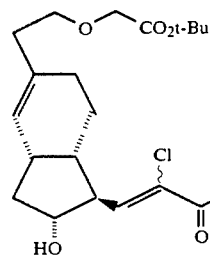

3-(3-oxa-4-tert butoxycarbonylbutyl)-7-exo-(2-chloro-4,4-dimethyl-3-oxo-1-nonen-6-ynyl)-8-endo-tetrahydroxypyranyloxy-cis-bicyclo[4.3.0]non-2-ene (5.70 g, 9.89 mmol) was dissolved in methanol (35.0 ml) and a catalytic amount of p-toluenesulfonic acid monohydrate was added thereto at room temperature. The mixture was stirred at the same temperature for 1.25 hour. To the reaction solution, a saturated sodium hydrogencarbonate aqueous solution was added. Then, methanol was distilled off under reduced pressure. The residual aqueous layer obtained was extracted with ethyl ether, and the organic layer was washed with water and a saturated sodium chloride aqueous solution and then dried over anhydrous magnesium sulfate. Then, the solvent was distilled off under reduced pressure, and the residue thereby obtained was purified by silica gel column chromatography (ethyl ether : n-hexane=2 : 3) to obtain 3-(3-oxa-4-tert-butoxycarbonylbutyl)-7-exo-(2-chloro-4,4-dimethyl-3-oxo-1-nonen66-ynyl)-8-endo-hydroxy-cis-bicyclo[4.3.0]non-2-ene (4.62 g, 94.8%) as a slightly yellow oily substance.

IRγmax(neat):3490, 2974, 2926, 1746, 1686, 1620, 1470 cm$^{-1}$.

NMR(CDCl$_3$)δ: 1.09 (3H, t, J=7.2Hz), 1.36 (6H, s), 1.47(9H, s), 2.52 (2H, t, J=2.0Hz), 3.60 (2H, t, J=7-2Hz), 3.92 (2H, s), 4.00 (1H, m), 5.40 (1H, brs), 6.32 (1H, d, J=9.2Hz).

EXAMPLE 19

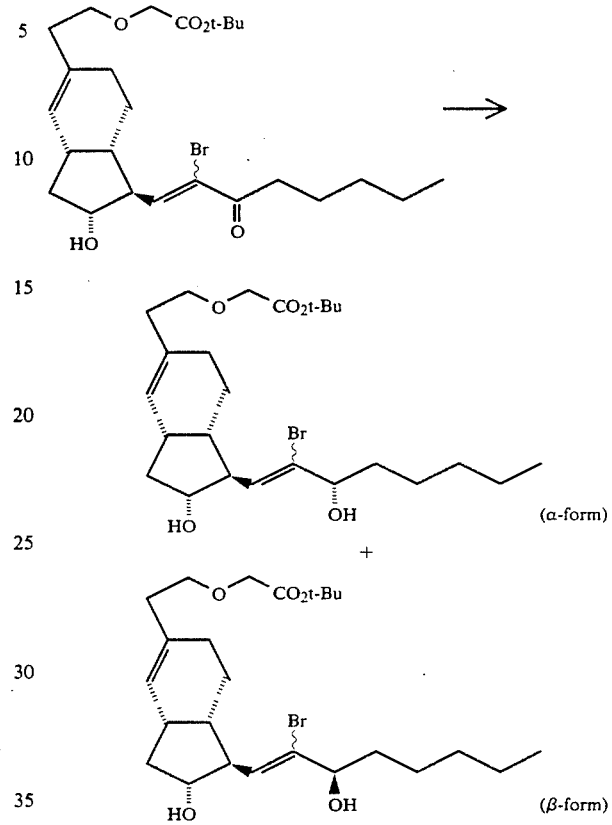

To a toluene solution (4 ml) of 2,6-di-tert-butyl-4-methylphenol (803 mg, 3.65 mmol), diisobutylaluminum hydride (1M toluene solution, 2.7 ml, 2.7 mmol) was gradually dropwise added under an argon atmosphere at a temperature of from −10° C. to −15° C. The mixture was stirred at the same temperature for one hour. Then, at −78° C., a toluene solution (6 ml) of 3-(3-oxa-4-tert-butoxycarbonylbutyl)-7-exo-(2-bromo-3-oxo-1-octenyl)-8-endo-hydroxy-cis-bicyclo[4.3.0]non-2-ene (130 mg, 0.26 mmol) was dropwise added thereto. The mixture was stirred at −78° C. for 40 minutes, and then the temperature was raised from −78° C. to −20° c over a period of 3 hours. To the reaction solution, a saturated sodium chloride aqueous solution was added, and the mixture was extracted with ethyl acetate. The organic layer was washed with water and a saturated sodium chloride aqueous solution and then dried over anhydrous magnesium sulfate. Then, the solvent was distilled off, and the residue thereby obtained was purified by silica gel column chromatography (n-hexane : ethyl ether=1 : 5) to obtain 3-(3-oxa-4-tert-butyoxycarbonylbutyl)-7-exo-(3α-hydroxy-2-bromo-1-octenyl)-8-endo-hydroxy-cis-bicyclo[4.3.0]non-2-ene (91 mg 70%) as a highly polar component and 3-(3-oxa-4-tert-butoxycarbonybutyl)-7-exo-(3β-hydroxy-2-bromo-1-octenyl)-8-endo-hydroxy-cis-bicyclo[4.3.0]non-2-ene (22 mg, 17%) as a low polar component, each as a colorless oily substance. The spectrum data of the α-epimer are shown below. The spectrum data of the β-epimer were substantially the same as the α-epimer.

IRγmax(neat): 3400, 2950, 1740, 1450 cm$^{-1}$.

NMR(CDCl3)δ: 0.90 (3H, t, J=7.2Hz), 1.44 (9H, s), 3.60 (2H, t, J=8.0Hz), 3.90 (1H, q, J=6.4Hz), 3.96 (2H, s), 4.12 (1H, t, J=4.8Hz), 5.40 (1H, bs), 5.86 (1H, d, J=9.2 Hz).

EXAMPLES 20 TO 26

In Table 5, the IR and NMR spectrum data of the α-epimer forms of the compounds prepared in the same manner as in Example 19 are presented. The spectrum data of the β-epimer forms were the same.

EXAMPLE 27

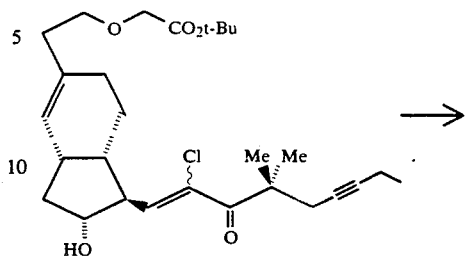

TABLE 5

| Example No. | $R^5$ | Yield (%) | IR$\nu_{max}$ (neat)cm$^{-1}$ | NMR (CDCl3)δ |
|---|---|---|---|---|
| 20 | Me⸜⸜⸜ H / alkyne-Et | α: 73 β: 20 | 3450, 2950, 1740, 1450, 1130. | 0.98(3H, d, J=6.0Hz), 1.10(3H, t, J=7.8Hz), 1.44 (9H, s), 2.85(1H, m), 3.58(2H, t, J=7.2Hz), 3.90 (2H, m), 3.94(2H, s), 5.38(1H, bs), 5.94(1H, d, J=9.0Hz). |
| 21 | Me⸜⸜⸜ Me / alkyne-Et | α: 53 β: 22 | 3450, 2950, 1750, 1450. | 1.06(3H, s), 1.10(3H, s), 1.16(3H, t, J=7.2Hz), 1.50 (9H, s), 2.90(1H, m), 3.62(2H, t, J=7.2Hz), 3.96(2H, s), 4.00(1H, m), 4.18(1H, s), 5.40(1H, bs), 5.84(1H, d J=8.8Hz). |
| 22 | Et-CH(—)-CH2CH2CH=CMe2 | α: 67 β: 16 | 3400, 2900, 1740, 1440. | 0.92(3H, d, J=7.2Hz), 1.45(9H, s), 1.60(3H, s), 1.68 (3H, s), 3.60(2H, t, J=7.2Hz), 3.92(2H, s), 4.16(1H, m 5.05(1H, m), 5.38(1H, bs), 5.82(1H, d, J=9.6Hz). |
| 23 | Me-CH(—)-O-Ph | α: 68 β: 5 | 3400, 2950, 2250, 1740, 1600, 1490, 1240. | 1.40(3H, d, J=7.8Hz), 1.50(9H, s), 3.60(2H, t, J=6.8 Hz), 3.96(2H, s), 4.32(1H, d, J=6.0Hz), 4.68(1H, m), 5.42(1H, bs), 6.05(1H, d, J=7.8Hz), 6.90–7.40(5H, m) |
| 24 | Me⸜⸜⸜ Me / C(—)-O-Ph | α: 48 β: 20 | 3400, 2900, 1740, 1590, 1490, 1220. | 1.28(3H, s), 1.30(3H, s), 1.44(9H, s), 2.90(1H, m), 3.60(2H, t, J=7.8Hz), 3.94(2H, s), 4.34(1H, m), 5.40 (1H, bs), 6.00(1H, d, J=10.0Hz), 6.94–7.40(5H, m). |
| 25 | Me⸜⸜⸜ Me / C(—)-O-C6H4-OCH3 | α: 60 β: 19 | 3400, 2900, 1740, 1580, 1490, 1220. | 1.28(6H, s), 1.44(9H, s), 2.95(1H, m), 3.62(2H, t, J=8.0Hz), 3.76(2H, s), 3.95(2H, s), 4.00(1H, m), 4.24 (1H, m), 5.40(1H, bs), 5.95(1H, d, J=9.2Hz), 6.94(4H, m). |
| 26 | cyclopentyl-CH2— | α: 63 β: 14 | 3408, 2928, 1748, 1450, 1368, 1226, 1130. | 1.45(9H, s), 3.59(2H, t, J=7.0Hz), 3.92(2H, s), 5.36 (1H, bs), 5.77(1H, d, J=10.0Hz). |

-continued

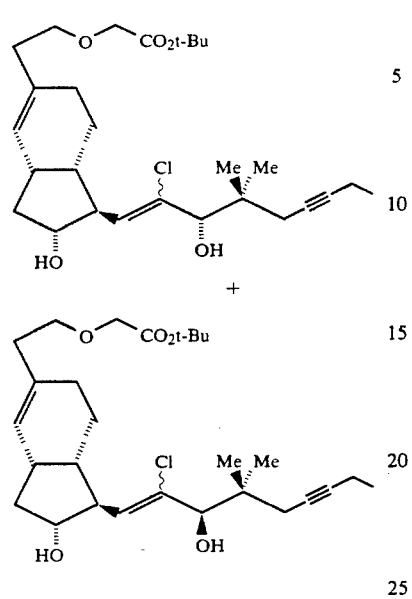

To a toluene solution (84.0 ml) of 2,6-di-tert-butyl-4-methylphenol (9.78 g, 44.5 mmol), diisobutylaluminum hydride (1.5M toluene solution, 18.5 ml, 27.8 mmol) was dropwise added over a period of 30 minutes under an argon atmosphere at 0° C. Then, the mixture was stirred at the same temperature for 90 minutes. Then, at −78° C., a toluene solution (30.0 ml) of 3-(3-oxa-4-tert-butoxycarbonylbutyl)-7-exo-(2-chloro-4,4-dimethyl-3-oxo-1-nonen-6-ynyl)-8-endo-hydroxy-cis-bicyclo[4.3.0]non-2-ene (1.37 g, 2.78 mmol) was dropwise added to the reaction solution over a period of 10 minutes. Then the temperature was raised from −78° C. to −60° C. over a period of two hours. To the reaction solution, a saturated sodium chloride aqueous solution was added, and the mixture was stirred for a while. Then, the mixture was extracted with ethyl acetate, and the organic layer was washed with water and a saturated sodium chloride aqueous solution and then dried over anhydrous magnesium sulfate. Then, the solvent was distilled off under reduced pressure, and the residue thereby obtained was purified by silica gel column chromatography (ethyl ether : n-hexane =1 : 1–2) to obtain 3-(3-oxa-4-tert-butoxycarbonylbutyl)-7-exo-(2-chloro-4,4-dimethyl-3α-hydroxy-1-nonen-6-ynyl)-8-endo-hydroxy-cis-bicyco[4.3.0]non-2-ene (1.18 g, 86.0%) as a highly porous component and 3-(3-oxa-4-tert-butoxycarbonylbutyl)-7-exo-(2-chloro-4,4-dimethyl-3β-hydroxy-1-nonen-6-ynyl)-8-endo-hydroxy-cis-bicyclo[4.3.0]non-2-ene (0.16 g, 11.6%) as a low polar component, each as a slightly yellow oily substance. The spectrum data of the α-epimer are shown below. The spectrum data of the β-epimer were substantially the same as α-epimer.

IRγmax(neat): 3454, 2974, 2920, 1743, 1395, 1371 cm$^{-1}$.

NMR(CDCl$_3$)δ: 1.01 (3H, s), 1.02 (3H, s), 1.11 (3H, t, J =7.2Hz), 1.43 (9H, s), 2.90 (1H, m), 3.57 (2H, t, J=7.2Hz), 3.90 (2H, s), 4.10 (2H, m), 5.37 (1H, brs), 5.58 (1H, d, J=9.2Hz).

EXAMPLE 9

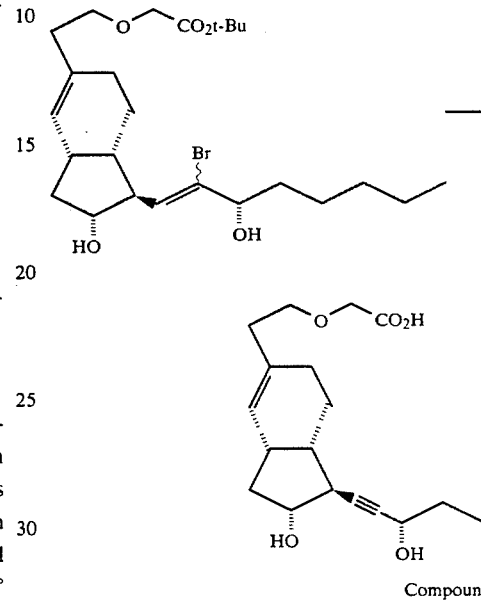

Compound (e)

Tetra-n-butyl ammonium hydrogen sulfate (183 mg, 0.54 mmol) was dissolved in water (0.1 ml). Then, an ethyl ether-toluene solution (2 : 1, 3 ml) of 3-(3-oxa-4-tert-butoxycarbonybutyl)-7-exo-(3α-hydroxy-2-bromo-1-octenyl)-8-endo-hydroxy-cis-bicyclo[4.3.0]non-2-ene (91 mg, 0.18 mmol) was added thereto. Then, a 50% sodium hydroxide aqueous solution (0.7 ml) was slowly dropwise added at 0° C., and the mixture was stirred at room temperature for 36 hours. To the reaction solution, water was added, and the pH was adjusted to 4 with a 5% hydrochloric acid aqueous solution. Then, the mixture was extracted with ethyl acetate, and the extract was washed with water and a saturated sodium chloride aqueous solution and then dried over anhydrous magnesium sulfate. Then, the solvent was distilled off to obtain 3-(3-oxa-4-carboxybutyl)-7-exo-(3α-hydroxy-1-octynyl)-8-endo-hydroxy-cis-bicyclo[4.3.0]-non-2-ene (compound (3e) 32.8 mg, 53.3%) as a colorless oily substance.

IRγmax(neat): 3400, 2950, 2220, 1740, 1450 cm$^{-1}$.

NMR(CDCl$_3$)δ: 0.90 (3H, t, J=7.2Hz), 3.60 (2H, t, J =8.0Hz), 4.04 (2H, s), 4.10 (1H, q, J =6.4Hz), 4.20 (1H, m), 4.70 (2H, m), 5.42 (1H, bs).

REFERENCE EXAMPLES 10 TO 16

In Table 6, the IR and NMR spectrum data of the compounds prepared in the same manner as in Reference Example 9 are presented.

TABLE 6

[Structure: bicyclic compound with OCH2COOH side chain, HO and OH hydroxyls, alkyne with R5 substituent]

| Reference Example No. | R⁵ | Yield (%) | IR $\nu_{max}$ (neat) cm$^{-1}$ | NMR (CDCl$_3$) δ |
|---|---|---|---|---|
| 10 (f) | Me,,,⟨H, C≡C-Et | 83.0 | 3400, 2950, 2220, 1740, 1440. | 1.02(3H, d, J=6.0Hz), 1.10(3H, t, J=7.8Hz), 3.60 (2H, t, J=7.2Hz), 4.02(2H, s), 4.10(1H, q, J=6.4Hz), 4.40(1H, dd, J=1.0, 4.0Hz), 4.70(2H, m), 5.40(1H, bs). |
| 11 (g) | Me,,,⟨Me, C≡C-Et | 76.0 | 3450, 2950, 2220, 1740. | 1.04(3H, s), 1.08(3H, s), 1.12(3H, t, J=7.2Hz), 3.60 (2H, t, J=7.2Hz), 4.04(2H, s), 4.10(3H, m), 4.26(1H, d, J=2.0Hz), 5.36(1H, bs). |
| 12 (h) | Et-CH-CH2CH2CH=CMe2 | 51.9 | 3400, 2950, 2200, 1730, 1440. | 0.96(3H, d, J=7.2Hz), 1.60(3H, s), 1.68(3H, s), 3.60 (2H, t, J=7.2Hz), 4.06(2H, s), 4.14(1H, m), 4.38(3H, m), 5.04(1H, m), 5.40(1H, bs). |
| 13 (i) | Me-CH-O-Ph | 61.0 | 3450, 2950, 2220, 1700, 1600, 1490, 1240. | 1.39(3H, d, J=7.8Hz), 3.58(2H, t, J=6.8Hz), 4.02(2H, s), 4.50(5H, m), 5.36(1H, bs), 6.90-7.20(5H, m). |
| 14 (j) | Me,,,C(Me)-O-Ph | 79.5 | 3400, 2900, 2220, 1730, 1590, 1490, 1220. | 1.32(3H, s), 1.38(3H, s), 3.62(2H, t, J=7.8Hz), 4.05 (2H, s), 4.16(1H, q, J=6.4Hz), 4.44(1H, d, J=2.0Hz), 4.54(3H, m), 5.40(1H, bs), 6.90-7.34(5H, m). |
| 15 (k) | Me,,,C(Me)-O-C6H4-OCH3 | 83.2 | 3400, 2950, 2200, 1730, 1590, 1490. | 1.32(3H, s), 1.38(3H, s), 3.62(2H, t, J=8.0Hz), 3.80 (3H, s), 4.04(2H, s), 4.16(1H, q, J=6.4Hz), 4.40(1H, d, J=3.2Hz), 4.56(3H, m), 5.40(1H, bs), 6.84(4H, m). |
| 16 (l) | CH2-cyclopentyl | 85.1 | 3376, 2932, 1736, 1218, 1038. | 3.30-3.80(3H, m), 4.03(2H, s), 5.36(1H, bs). |

REFERENCE EXAMPLE 17

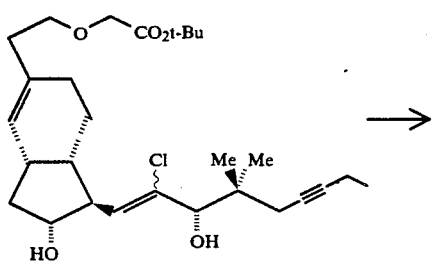

→

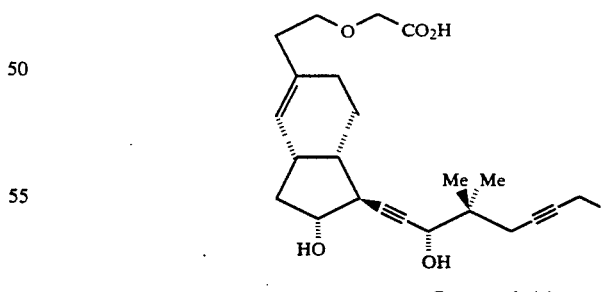

Compounds (g)

Purified water (40 drops) was added to tetra-n-butyl ammonium hydrogen sulfate (6.92 g, 20.0 mmol) to obtain a paste. To this paste, a toluene solution (40.0 ml) of 3-(3-oxa-4-tert-butoxycarbonylbutyl)-7-exo-(2-chloro-4,4-dimethyl-3α-hydroxy-1-nonen-6-ynyl)-8-endo-hydroxy-cis-cis-bicyclo[4.3.0]non-2-ene (1.01 g, 2.04 mmol) was added, and then a 50% sodium hydroxide aqueous solution (32.0 ml, 400 mmol) was dropwise added at 0° C. The mixture was stirred at 60° C. for 12 hours. After cooling the reaction solution, water was added thereto, and the pH was adjusted to 4 with a 10% hydrochloric acid aqueous solution. Then, the mixture was extracted with ethyl acetate, and the organic layer was washed sequentially with a 5% hydrochloric acid aqueous solution, water and a saturated sodium chloride aqueous solution and then dried over anhydrous magnesium sulfate. Then, the solvent was distilled off under reduced pressure, and the residue thereby obtained was purified by silica gel column chromatography (chloroform : methanol : acetic acid = 200 : 8 : 1) to obtain 3-(3-oxa-4-carboxybutyl)-7-exo-(4,4-dimethyl-3α-hydroxy-1,6-nondiynyl)-8-endo-hydroxy-cisbicyclo[4.3.0]non-2-ene (compound (g), 655 mg, 79.9%) as a colorless oily substance.

IR$\gamma$max(neat): 3450, 2950, 2920, 200, 1740, 1434, 1320 cm$^{-1}$.

NMR(CDCl$_3$)$\delta$: 1.04 (3H, s), 1.08 (3H, s), 1.12 (3H, t, J = 7.2Hz), 3.60 (2H, t, J = 7.2Hz), 4.04 (2H, s), 4.10 (3H, m), 4.26 (1H, d, J = 2.0Hz), 5.36 (1H, brs), 4.70 (2H, m), 5.42 (1H, bs).

TEST EXAMPLE 1: PLATELET ANTI-AGGREGATORY ACTIVITIES

Japanese white male rabbits having a weight of from 2.0 to 2.5 kg were used.

Under anesthesia with pentobarbital sodium, blood was collected from the carotid artery and mixed with citric acid dextrose solution (1/7 volume) as an anticoagulant. Then, the mixture was subjected to centrifugal separation at 140 ×g for 15 minutes, whereupon the supernatant (platelet rich plasma: PRP) was collected. PRP was subjected to centrifugal separation at 1,300 ×g for 7 minutes, and platelet pellets thereby obtained were washed with a HEPES buffer solution (pH 6.5) for washing platelets and then subjected to centrifugal separation at 1,300 ×g for 7 minutes. The platelet pellets were washed twice under the same conditions and then suspended in a suspending solution (prepared by adding 0.1% human solution for washing platelets) to make a platelet suspension containing from 5 to 8 × 10$^8$ platelets/ml. An aggregation meter was used for the measurement of the platelet aggregatory ability. To 380 $\mu$l of the platelet suspension, 10 $\mu$l of a test compound or a solvent as control was added. Three minutes later, 10 $\mu$l of a platelet aggregatory substance (as the final concentration: 10M ADP, or 1 $\mu$g/kg of collagen) was added to induce platelet aggregation. The blood platelet anti-aggregatory activities by the test compound was represented by ED$_{50}$ (i.e. the concentration of the test compound inhibiting 50% of the platelet aggregation). The results are shown in Table 7.

TABLE 7

| Platelet anti-aggregatory activities ED$_{50}$ (M) | | |
|---|---|---|
| Compound | ADP (activity ratio) | Collagen (activity ratio) |
| PGI$_2$ | 2.9 × 10$^{-9}$ (1) | 3.4 × 10$^{-9}$ (1) |
| c | 1.3 × 10$^{-9}$ (2.2) | 5.8 × 10$^{-10}$ (5.9) |
| g | 2.7 × 10$^{-9}$ (1.1) | 8.6 × 10$^{-9}$ (1/2.5) |
| h | 5.4 × 10$^{-9}$ (1/1.9) | 3.4 × 10$^{-9}$ (1) |

TEST EXAMPLE 2: INHIBITORY EFFECT ON FORMATION OF GASTRIC LESION INDUCED BY ETHANOL

Male wistar rats having a weight of from 170 to 270 g were put into individual cages and starved for 24 hours. During this starvation period, the rats were allowed to drink water freely. A test compound or PGE$_2$ as a comparative compound was orally administered at a dose of 3 $\mu$g/kg, 10 $\mu$g/kg or 30 $\mu$g/kg, and 30 minutes later, 1 ml of 99.5% ethanol was orally administered to each rat. One hour or 4.5 hours after the ethanol administration, each rat was sacrificed by cervical vertebral dislocation, and the stomach was taken out. Each stomach was inflated with an amount of about 8 ml of 1% formaline solution and put into 1% formaline solution for 30 minutes to fix the gastric wall. After the fixing, the stomach was severed along the greater curvature, and the mucous membrane surface of the stomach was gently washed with flowing water. Then, the total length of lesions appearing on the gastric glandular portion was determined and used as the ulcer index.

The inhibitory effect of the test compound was represent by ED$_{50}$ (i.e. the dose of the test compound at which the ulcer was inhibited by 50% relative to the ulcer index of the non-treated group). The results are shown in Table 8. To the non-treated group, the solvent was administered.

TABLE 8

| Inhibitory effect on formation of gastric lesion induced by ethanol ED$_{50}$ ($\mu$g/kg, p.o) | |
|---|---|
| Compound | 1.5 hours later (activity ratio) |
| PGE$_2$ | 9.03 (1) |
| c | 0.97 (9.3) |
| f | 2.1 (4.3) |
| h | 12.7 (1/1.4) |

Now, Formulation Examples for the formulation of compounds used in the preceding Test Examples, will be given.

FORMULATION EXAMPLE 1

Compound: 500 mg
Potato starch: 150 mg
Silicic anhydride: 50 mg
Magnesium stearate: 10 mg
Lactose: Balance to the total of 1,000 mg The above ingredients were uniformly mixed and filled into hard capsules in an amount of 200 mg each.

FORMULATION EXAMPLE 2

Compound: 500 mg
Potato Starch: 100 mg
Crystalline cellulose: 60 mg
Silicic anhydride: 50 mg
Hydroxypropyl cellulose: 30 mg
Magnesium Stearate: 15 mg
Lactose: Balance to the total of 1,000 mg The active ingredients, lactose, potato starch, crystalline cellulose and silicic anhydride were mixed. After an addition of a methanol solution containing 10% of hydroxypropyl cellulose was added thereto, and the mixture was kneaded and granulated. Then, it was extruded through a screen having openings with a diameter of 0.8 mm, to obtain granules. After drying the granules, the magnesium stearate was added thereto, followed by compression molding to obtain tablets each having a weight of 200 mg.

FORMULATION EXAMPLE 3

Compound: 500 mg
Propylene glycol: Balance to the total of 10 ml

The active ingredient was dissolved in propylene glycol, and the solution was asceptically filtered and then filled into ampules in an amount of 0.2 ml each.

FORMULATION EXAMPLE 4

Compound: 250 mg
Polyethylene glycol 1,500: 3,000 mg
Polyethylene glycol 6,000: Balance to the total of 5,000 mg The above ingredients were heat-melted at 60° C. and uniformly mixed, and the mixture was poured into a plastic mold and cooled to obtain a suppository of 1 g.

We claim:

1. A cis-bicyclo[4.3.0]non-2-ene derivative of the formula:

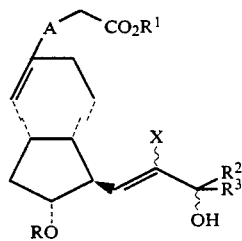

(I)

wherein R is a hydrogen atom, or a protecting group for a hydroxyl group, $R^1$ is a hydrogen atom, a $C_1$-$C_{12}$ straight or branched chain alkyl group, a substituted or unsubstituted phenyl group, a $C_6$-$C_{12}$ aralkyl group containing a condensed aromatic ring or an aromatic hetero ring, or 1 equivalent of a cation, A is —CH= CH—$CH_2$—, or —$CH_2$—$CH_2$—O—, $R^2$ is a $C_3$—$C_{10}$ straight or branched chain alkyl group, a $C_1$-$C_3$ alkyl group substituted by an aryloxy group which may be substituted, a $C_3$-$C_{12}$ straight or branched chain alkenyl group, a $C_3$-$C_8$ straight or branched chain alkynyl group, or a $C_1$-$C_3$ alkyl group substituted by a phenyl or phenoxy group which may be substituted, by a $C_1$-$C_6$ alkoxy group or by a $C_5$-$C_8$ cycloalkyl group, $R^3$ is a hydrogen atom, a methyl group, or a vinyl group, and X is a halogen atom.

2. A cis-bicyclo[4.3.0]non-2-ene derivative of the formula:

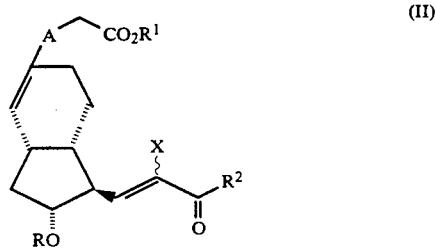

(II)

wherein R is a hydrogen atom, or a protecting group for a hydroxyl group, $R^1$ is a hydrogen atom, a $C_1$-$C_{12}$ straight or branched chain alkyl group, a substituted or unsubstituted phenyl group, a $C_6$-$C_{12}$ aralkyl group containing a condensed aromatic ring or an aromatic hetero ring, or 1 equivalent of a cation, A is —CH= CH—$CH_2$—, or —$CH_2$—$CH_2$—O—, $R^2$ is a $C_3$-$C_{10}$ straight or branched chain alkyl group, a $C_1$-$C_3$ alkyl group substituted by an aryloxy group which may be substituted, a $C_3$-$C_{12}$ straight or branched chain alkenyl group, a $C_3$-$C_8$ straight or branched chain alkynyl group, or a $C_1$-$C_3$ alkyl group substituted by a phenyl or phenoxy group which may be substituted, by a $C_1$-$C_6$ alkoxy group or by a $C_5$-$C_8$ cycloalkyl group, and X is a halogen atom.

* * * * *

UNITED STATES PATENT AND TRADEMARK OFFICE
CERTIFICATE OF CORRECTION

PATENT NO.   :   5,117,037
DATED        :   May 26, 1992
INVENTOR(S)  :   Masakatsu Shibasaki et al.

It is certified that error appears in the above-identified patent and that said Letters Patent is hereby corrected as shown below:

On the title page: Item [75]

The second inventor's name is incorrect, should be,

--Atsuo Takahashi--, and the title is incorrect, should be,

--CIS-BICYCLO(4.3.0)NON-2-ENE DERIVATIVES--.

Signed and Sealed this

Thirteenth Day of July, 1993

Attest:

MICHAEL K. KIRK

*Attesting Officer*      Acting Commissioner of Patents and Trademarks